(12) United States Patent
Aguilera Suárez et al.

(10) Patent No.: US 9,895,362 B2
(45) Date of Patent: Feb. 20, 2018

(54) PHARMACEUTICAL COMPOSITION COMBINING AN ANTICONVULSANT AND A DERIVATE OF NICOTINIC ACID

(71) Applicant: Farmacéuticos Rayere, S.A., México, D.F. (MX)

(72) Inventors: Graciela de los Ángeles Aguilera Suárez, Distrito Federal (MX); Carmen Miguel Gómez Sánchez, México, D. F. (MX); Martha Rosaura Juárez Lora, México, D. F. (MX)

(73) Assignee: FARMACÉUTICOS RAYERE, S.A., México, D.F. (MX)

( * ) Notice: Subject to any disclaimer, the term of this patent is extended or adjusted under 35 U.S.C. 154(b) by 0 days.

(21) Appl. No.: 15/319,287

(22) PCT Filed: Jun. 16, 2014

(86) PCT No.: PCT/MX2014/000091
§ 371 (c)(1),
(2) Date: Dec. 15, 2016

(87) PCT Pub. No.: WO2015/194926
PCT Pub. Date: Dec. 23, 2015

(65) Prior Publication Data
US 2017/0151223 A1 Jun. 1, 2017

(51) Int. Cl.
  *A61K 31/195* (2006.01)
  *A61K 31/455* (2006.01)
  *A61K 9/00* (2006.01)

(52) U.S. Cl.
  CPC .......... *A61K 31/455* (2013.01); *A61K 9/0019* (2013.01); *A61K 31/195* (2013.01)

(58) Field of Classification Search
  CPC ........................ A61K 31/455; A61K 31/195
  See application file for complete search history.

(56) References Cited

U.S. PATENT DOCUMENTS 6,451,857 B1 9/2002 Hurtt et al.
2008/0269310 A1 10/2008 Foster

FOREIGN PATENT DOCUMENTS

| MX | 288732 | 7/2011 |
| WO | 2007083985 A1 | 7/2007 |
| WO | 2007148950 A1 | 12/2007 |
| WO | 2008077599 A1 | 7/2008 |

OTHER PUBLICATIONS

Ahlgren, S.C. et al., Mechanical Hyperalgesia in Streptozotocin-Diabetic Rats, Neuroscience, 1993, pp. 1049-1055, vol. 52, No. 4.
Attal, N. et al., Pharmacological Management of Neuropathic Pain, IASP International Association for the Study of Pain, Nov. 2010, vol. XVIII, Issue 9.
Bouhassira, D. et al., Prevalence of Chronic Pain With Neuropathic Characteristics in the General Population, IASP International Association for the Study of Pain, 2008, pp. 380-387, 136.
Chaparro, L.E. et al., Pharmacotherapy for the Prevention of Chronic Pain After Surgery in Adults, Cochrane Database of Systematic Reviews, 2013, Issue 7.
Decosterd, I. et al., Spared Nerve Injury: An Animal Model of Persistent Peripheral Neuropathic Pain, IASP International Association for the Study of Pain, 2000, pp. 149-158, 87.
Digirolamo, G. et al., Effects of Cyclooxygenase Inhibitor Pretreatment on Nitric Oxide Production, nNOS and iNOS Expression in Rat Cerebellum, British Journal of Pharmacology, 2003, pp. 1164-1170, 139.
Dworkin, R. et al., Recommendations for the Pharmacological Management of Neuropathic Pain: An Overview and Literature Update, Mayo Clinic Proceedings, Mar. 2010, pp. S3-S14, 85.
Finnerup, N. et al., The Evidence for Pharmacological Treatment of Neuropathic Pain, IASP International Association for the Study of Pain, 2010, pp. 573-581, 150.
Gordh, T. et al., Gabapentin in Traumatic Nerve Injury Pain: A Randomized, Double-Blind, Placebo-Controlled, Cross-Over, Multi-Center Study, IASP International Association for the Study of Pain, 2008, pp. 255-266, 138.
Green, R. et al., AGA Technical Review on the Evaluation of Liver Chemistry Tests, Gastroenterology, 2002, pp. 1367-1384, 123.
Kusunose, N. et al., Molecular Basis for the Dosing Time-Dependency of Anti-Allodynic Effects of Gabapentin in a Mouse Model of Neuropathic Pain, Molecular Pain, 2010.
Lenzen, S., The Mechanisms of Alloxan-and Streptozotocin-Induced Diabetes, Diebetologia, 2008, pp. 216-226, 51.
Moore, et al., Gabapentin for Chronic Neuropathic Pain and Fibromyalgia in Adults, Cochrane Database Syst Rev, Sep. 22, 2014.
Schmidtko, A., et al., No NO, no pain? The role of nitric oxide and cGMP in spinal pain processing, Trends in Neuroscience, 2009, pp. 3393-346. vol. 32, No. 6.
Straube, S. et al., Single Dose Oral Gabapentin for Established Acute Postoperative Pain in Adults, Cochrane Database Syst Rev, Sep. 22, 2014.
Szkudelski, T., The Mechanism of Alloxan and Streptozotocin Action in B Cells of the Rat Pancreas, Physiological Research, 2001, pp. 536-546, vol. 50.
Tao, F. et al., Differential Roles of Neuronal and Endothelial Nitric Oxide Synthases During Carrageenan-Induced Inflammatory Hyperalgesia, Neuroscience, 2004, pp. 421-430, 128.

(Continued)

*Primary Examiner* — James D. Anderson
(74) *Attorney, Agent, or Firm* — Standley Law Group LLP

(57) ABSTRACT

The combination of gabapentin with lysine clonixinate (CLG) makes it possible to relieve neuropathic pain caused both by diabetic neuropathy and by an injury to the nerve. The CLG combination produces a synergy in the antiallodynic effect, when the allodynia has been generated by direct mechanical damage to nervous tissue or when it has been produced as a result of a diabetic pathology. The therapeutic effect of the CLG combination is 3 to 11 times greater than the effect of each of the drugs separately.
The CLG combination is safe, because it shows no adverse effects on motor activity or alterations in neurological parameters nor damage to the liver or kidney.

12 Claims, 7 Drawing Sheets

(56) References Cited

OTHER PUBLICATIONS

Tesfaye, S. et al., Diabetic Neuropathies: Update on Definitions, Diagnostic Criteria, Estimation of Severity, and Treatments, Diabetes Care, Oct. 2010, pp. 2285-2293, vol. 33, No. 10.
Tesfaye, S. et al., Painful Diabetic Peripheral Neuropathy: Consensus Recommendations on Diagnosis, Assessment and Management, Metabolism Research and Reviews, 2011, pp. 619-638, 27.
Treede, R. et al., Neuropathic Pain: Redefinition and A Grading System for Clinical and Research Purposes, Neurology, Apr. 29, 2008, 99 1630-1635, 70.
Vivinik, A. et al., Guidelines in the Management of Diabetic Nerve Pain: Clinical Utility of Pregabalin, Diabetes, Metabolic Syndrome and Obesity: Targets and Therapy, Feb. 23, 2013, pp. 57-78.
Von Hehn, C. et al., Deconstructing the Neuropathic Pain Phenotype to Reveal Neural Mechanisms, Neuron, Feb. 23, 2012, pp. 638-652.
Winter, C. et al., Carrageenin-Induced Edema in Hind Paw of the Rat as an Assay for Antiinflammatory Drugs, Antiinflamatory Assay, 1962, pp. 544-547.
Woolf, C., Pain: Moving from Symptom Control Toward Mechanism-Specific Pharmacologic Management, Ann. Intern. Med., 2004, pp. 441-451, 140.
Yoon, M. et al., Evaluation of Interaction between Gabpentin and Ibuprofen on the Formalin Test in Rats, Anesthesiology, 1999; pp. 1006-1113, vol. 91, No. 4.
Zimmerman, M., Ethical Guidelines for Investigation of Experimental Pain in Conscious Animals, Pain, 1983, pp. 109-110.

Gabapentin

CL

PHARMACEUTICAL COMPOSITION COMBINING AN ANTICONVULSANT AND A DERIVATE OF NICOTINIC ACID

DESCRIPTION OF THE INVENTION

This invention relates to pharmaceutical compositions that contain two active principles, one of them being an anticonvulsant, gabapentin, and the other, a nicotinic acid derivative, lysine clonixinate. Gabapentin, referred to in the present invention, is 2-[1-(aminomethyl)cyclohexyl] acetic acid and has a molecular weight of 171.24. Its structural formula is shown in FIG. 1. Lysine clonixinate, referred to in the present invention, is the lysine salt of 2-[(3-chloro-2-methylphenyl) amino]-3-pryridinecarboxylic acid and belongs to the group of nicotinic acid derivatives. Its molecular weight is 408.88, and its structural formula is shown in FIG. 2.

The combination of gabapentin with lysine clonixinate (CLG) in specific proportions makes it possible to relieve neuropathic pain caused both by diabetic neuropathy and by nerve injury. The CLG combination results in superadditivity (synergy) of the pharmacological effects of each of the drugs separately.

BACKGROUND

Neuropathic pain has been defined as "a pain that occurs as a direct result of an injury or a disease that directly affects the somatosensory system" (Treede, R. D., Jensen, T. S., Campbell, J. N., et al., 2008). This type of pain differs from nociceptive, somatic or visceral pain, because the latter occurs in non-nerve tissue and is caused either by a mechanical injury or damage caused internally by some pathology. Nociceptive pain is usually associated with an inflammatory process following tissue damage, and as a result reversible adaptive changes occur in the sensory nervous system. This leads to hypersensibility to pain, which is a protective mechanism that alerts and prevents subsequent damage at the site of injury, ensuring adequate repair of the damaged tissue. This painful sensation is mediated in the periphery by primary sensory neurons of high threshold, the so-called nociceptors, which transmit information to the brain through nociceptive pathways of the spinal cord. In this case, neither the structure nor the function of the nervous system is damaged, and the pain disappears when the damaged tissue has been repaired. Unlike this mechanism of damage→pain/inflammation→tissue repair→absence of pain, in the case of neuropathic pain, this occurs because it is one's own central or peripheral nervous system that directly receives the damage. This leads to morphological and functional changes in the sensory pathways that may become persistent without the pain disappearing. Once the damage to the nervous system is established, the natural mechanism of pain transmission is affected. This can cause pain to occur spontaneously and/or its threshold dramatically drops in such a way that the response to a pain stimulus is amplified both in amplitude and duration (hyperalgesia), or a normally harmless stimulus becomes painful (allodynia). Unlike somatic or visceral pain, when nerve damage occurs, the neural changes in susceptible individuals can be irreversible. Once established, neuropathic pain can be considered the manifestation of pathological neural plasticity that manifests itself as a state of autonomic disease of the nervous system that controls itself (von Hehn C. A., Baron, R., Woolf, C. J., 2012).

Within the etiology of neuropathic pain are physical injuries like trauma, resection or compression of the dorsal roots of the spinal cord, metabolic disorders like diabetes mellitus or vitamin B deficiency, some infections like those caused by varicella-zoster virus or HIV, neurotoxins like alcohol, or chemotherapy.

Diabetic Neuropathy

Peripheral diabetic neuropathy is a common complication of diabetes, presents itself as a variety of syndromes, among which is sensorimotor diabetic polyneuropathy (SMDPN), a very common condition affecting between 25% and 30% of diabetic patients. SMDPN is attributed to peripheral nerve damage due to metabolic and microvascular alterations as a result of chronic hyperglycemic exposure (diabetes) associated with cardiovascular risk factors (Tesfaye, S., Boulton, A. J., Dyck, P. J., et al., 2010).

Neuropathy Due to Traumatic or Postsurgical Neural Injury

When there is a mechanical injury to the peripheral nerve, the resulting pain is due to spontaneous activity generated in any site along the nociceptive pathway. However, more often, the spontaneous sensations that occur as a result of injury to the peripheral nerves are generated as a result of hyperexcitability of primary sensory neurons.

After the occurrence of a nerve injury, ectopic nervous activity is the main cause of the spontaneous sensations of pain, paresthesia or dysesthesia. The pain may be episodic or continuous, superficial or deep, and frequently presents itself as shooting pain of burning type (von Hehn, C. A., Baron, R., Woolf, C. J., 2012).

The prevalence of neuropathic pain indicates that it occurs in about 7% of the world's population (Bouhassira, D., Lanteri-Minet, M., Attal, N., Laurent, B., et al., 2008). However, the management of patients with chronic neuropathic pain is complex, and many patients do not respond to treatment, obtaining only partial pain relief, or they experience intolerable adverse effects.

For the treatment of neuropathic pain, common painkillers are generally inadequate. There is a practice that consists of giving patients pharmacological therapies at regular intervals, and effective pain treatment must be considered a favorable balance between pain relief and side effects, which not does necessarily imply having maximum analgesic effect (Vinik, A. and Casellini, C., 2013). It has been recommended to pay special attention to the following general considerations in pharmacotherapy for neuropathic pain:

For each patient, the effective and appropriate drug should be identified and its dose carefully adjusted based on its efficacy and the adverse effects it produces.

Lack of analgesic efficacy should be decided 2 to 4 weeks after treatment using an appropriate dose.

Based on the evidence of different clinical studies, any analgesic monotherapy only achieves approximately 50% of the maximum response. Therefore, it is suggested that a combination of analgesics may be very useful.

Gabapentin

Gabapentin is a structural analog of gamma aminobutyric acid (GABA), which, unlike this neurotransmitter, has an anticonvulsant effect that is not due to binding of the $GABA_A$ or $GABA_B$ receptors in the central nervous system (CNS). Gabapentin binds on the α2-δ site of the voltage-dependent calcium channels and modulates calcium input with a reduction of excitatory neurotransmission and, as a result, a decrease in the activation of the glutamate receptor and therefore a decrease in the pain signal (Dworkin, R., O'Connor, A., Audette, J., et al., 2010). So, in accordance with this mechanism of action, gabapentin, in addition to acting as an anticonvulsant, has the property of reducing the transmission of pain signals in the CNS.

The International Association for the Study of Pain has published, among others, a document for the pharmacological treatment of neuropathic pain (Attal, N. and Finnerup, N. B., 2010). In this publication, it is recommended to use specific medications that are classified into three groups: those of first line of choice, those of second line and those of third line. First line drugs are those that have been used in multiple randomized controlled clinical trials and have consistently shown their efficacy in the treatment of neuropathic pain. Among the drugs in this group is gabapentin.

Gabapentin has demonstrated efficacy in peripheral diabetic neuropathy (Finnerup, N. B., Sindrup, S. H., Jensen, T. S., 2010), in post-herpetic neuralgia (Moore, R. A., Wiffen, P., Derry, S., and McQuay, H., 2014, and Straube, S., Derry S., Moore, F. Wiffen P., and McQuay, J., 2014) and in neuropathic pain due to traumatic nerve injury (Gordh, T. E., Stubhaug, A., Jensen, T. S., et al., 2008). In the same way, in the "Treatment Guidelines for Neuropathic Pain" drawn up by the Toronto Consensus Panel, gabapentin has been classified among the first-line drugs for pain treatment in cases of peripheral diabetic neuropathy (Tesfaye, S., Vileikyte, L., Rayman, G., et al., 2011).

Lysine Clonixinate

Lysine clonixinate is an analgesic whose best known function is the inhibition of the cyclooxygenase enzymes (COX-1 and COX-2) responsible for the synthesis of prostaglandins (PGs). PGs are potent hyperalgesic mediators that modulate the signals that are transmitted along the pain pathway, increasing both transduction (peripheral sensitizing effect) and transmission (central sensitizing effect) of the pain stimulus. Therefore, inhibition of PG synthesis, both on the peripheral level and in the CNS, results in a reduction of the pain.

In addition to inhibiting the synthesis of prostaglandins, another of the effects of lysine clonixinate in the CNS that has been studied is the reduction in levels of neuronal nitric oxide synthase enzymes (NOSn) and induced enzymes (NOSi) (DiGirolamo, G., Farina, M., Ribeiro, M. L., et al., 2003). These enzymes belong to the family of nitric oxide synthases, which catalyze the production of nitric oxide (NO) from L-arginine. NO is a bioactive free radical that takes part in different physiological and pathological processes in many organs including the brain, the spinal cord and the nerves. The forms NOSn and NOSe (endothelial nitric oxide synthase) are expressed constitutively, producing NO in low concentrations. In these conditions, NO has a role in neurotransmission and vasodilatation. For its part, the expression of NOSi takes place as a response of the immune system to aggression against the body by parasites, bacterial infection, tumor growth and physical injury.

Once NOSi expression starts, this enzyme produces large quantities of NO for long periods of time, which leads to high concentrations of this and other molecules that generate high oxidizing power and severe toxicity, such as peroxynitrile, nitric dioxide and others. In particular, NO and cyclic guanosine monophosphate (cGMP) are important mediators in the neurochemical signal pathways in the spinal cord that contribute to raising the awareness of pain involved in the nociceptive process (Woolf, C. J., 2004).

Various studies have demonstrated that when peripheral nerve damage occurs, either through injury or some pathology like diabetes, the associated local inflammation and neuropathic pain that are produced are related to the production of NO by the expression of NOSi. It has also been shown that, on the level of the spinal cord, NO is involved in the development of hyperalgesia and inflammation in states of neuropathic pain (Schmidtko, A., Tegeder, I. and Geisslinger, G., 2009, and Tao, F., Tao, Y. X., Zhao, C., et al., 2004). Therefore, a reduction in iNOS levels due to the effect of lysine clonixinate could be important to reduce the progression of neuronal damage associated with neuropathic pain.

Combinations for Neuropathic Pain

For the purpose of finding the best treatment for neuropathic pain, several controlled clinical studies have been done using different medicines such as vasodilators, glutamate receptor antagonists, adrenoreceptor-α2 agonists, antidepressants and adrenergic receptor inhibitors. However, as mentioned above, the evidence indicates that only approximately 50% of the maximum response is achieved for any analgesic monotherapy, and increasing the dose is not recommended due to the increase in adverse effects. In clinical practice, 2 or more drugs are often used in combination in order to achieve some beneficial additive effect. With this objective, studies have been done using combinations of drugs for the treatment of neuropathic pain. A meta-analysis included 21 clinical studies with 1,972 participants and evaluated different combinations. It found that, of all studies included, only a comparison was possible, that is, gabapentin plus opioid versus gabapentin alone in two studies with 386 participants (Chaparro, L., Wiffen, P., Moore, R., et al., 2013). Analysis of the results of these two studies showed a modest but statistically significant superiority of the combination gabapentin plus opioid over gabapentin alone. However, this combination also produced more frequent discontinuation of the combined treatment (related to adverse effects) compared with the treatment with gabapentin alone.

The result of these and other studies is due to the fact that most of the combinations evaluated used drugs that share some effect associated with depression of the central nervous system (CNS), such as sedation or some type of cognitive dysfunction. This leads to an increase of this type of adverse effects. Consequently, an increase in the frequency of discontinuation of treatment frequently occurs, and therefore the usefulness of these combinations is very limited.

Gabapentin/Lysine Clonixinate

Given the apparent impact of the effects caused by the combination of drugs with similar profiles of adverse events, in particular in regard to CNS depression, combinations of drugs whose adverse effects are not of the same type are more favorable. In addition, the analgesic effect is increased in such a way that it is possible to reduce the content of each drug in combination compared to the drug administered separately. In particular, if medications in combination act on different sites of pain pathways or modulate different neurotransmission systems, the benefit would be to increase the level of analgesia while decreasing adverse events.

In the studies that support the present invention, it was noted that when lysine clonixinate is combined with gabapentin in specific proportions, the combination produces pharmacological effects of analgesia that indicate superadditivity (synergy) in the models of neuropathic pain associated with diabetes mellitus and by direct mechanical injury to the nerve. The foregoing makes it possible to decrease the therapeutic dose of the drugs in comparison with those that are used for each one when administered separately.

State of the Art

Patent MX 288732, "Pharmaceutical Composition Comprising a Nonsteroidal Anti-inflammatory Agent and an Anticonvulsant Agent," describes a pharmaceutical composition composed of the combination of Gabapentin and Meloxicam (7.5 and 300 mg, respectively), in a single dosage unit, for the treatment of neuropathic pain caused by various etiologies. The description of the patent refers to studies in rats, where pain and inflammation are caused by injecting carrageenan in the leg. This pain model evaluates somatic/inflammatory pain and has been described since 1962 to validate analgesic-anti-inflammatory drugs (Winter, C. A., Risley, E. A. and Nuss, G. W., 1962). It has been used until now. In this model, the damage is not to the nerve and the pain evaluated is not of the neuropathic type. Therefore, claim number 5 of the document is not valid. Furthermore, the published patent does not include figures, drawings or tables with experimental data to show that the experiments referred to in the description were actually performed.

The publication "Evaluation of Interaction between Gabapentin and Ibuprofen on the Formalin Test in Rats" (Yoon, M., Yaksh, T., 1999) describes the combination of gabapentin and ibuprofen on a model of non-neuropathic somatic pain (injection of formalin). It also shows a solely additive effect, since the experimental $DE_{50}$ (effective dose that provides an analgesic effect of 50%) did out turn out to be significantly different from the theoretical $DE_{50}$, which indicates a non-synergistic additive interaction between these drugs. Furthermore, the use of this combination therapy for neuropathic pain is not mentioned or demonstrated.

U.S. Pat. No. 6,451,857 (EP 1011658), "Analgesic compositions comprising anti-epileptic compounds and methods of using same," describes combinations of one or more antiepileptic drugs with a drug selected from the group of NMDA or NSAIDS receptor antagonists, for the relief of pain in mammals. In the description, the model of pain by injection of carrageenan is mentioned, and the examples specify the combination of gabapentin and naproxen. In the claims, pregabalin in combination is mentioned, and it does not mention that it is a combination to relieve neuropathic type pain.

The publication WO 2008/077599, "Combination Therapy of Lower Urinary Tract Disorders With α2δ Ligands and NSAIDS," claims the combination of gabapentin and an NSAID that can be celecoxib, diclofenac, diflunisal, flurbiprofen, naproxen, nimesulide or sulindac for the monotherapy treatment of urinary incontinence. None of the claims mention the treatment of neuropathic pain.

The publication WO 2006123247 A2, "Synergistic combinations of non-steroidal antiinflammatory drugs with alpha-delta-ligands," mentions combinations of non-steroidal anti-inflammatory drugs, particularly carprofen, with gabapentin and pregabalin for the treatment of pain and/or inflammation, particularly in dogs, cats and horses. The claims do not mention the treatment of neuropathic pain.

BRIEF DESCRIPTION OF THE DRAWINGS

A better understanding of the invention will be had from the appended drawings, in which.

Experimental Design

To assess the pharmacological efficacy of the CLG combination, two experimental models in mice were used: 1) Model of pain due to diabetic neuropathy induced with streptozotocin and 2) experimental model of neuropathic pain due to injury of the sciatic nerve.

In both models, the neuropathic pain was recorded by measuring the level of mechanical allodynia, using for this purpose the Von Frey filaments assay. Later, the analgesic interaction between gabapentin and lysine clonixinate was determined through isobolographic analysis for determination of addition, antagonism or synergism of the antiallodynic effect.

Finally, the toxicity of gabapentin, lysine clonixinate and their combination was determined, through studies evaluating motor activity and neurological profile and monitoring the levels of hepatic and renal function markers.

All the experiments described below were carried out in accordance with current guidelines for the care of laboratory animals and the ethical guidelines for experimental research on pain in animals suggested by M. Zimmermann (1983).

EXAMPLE I

Analgesia of the CLG Combination in Diabetic Neuropathy

The use of chemical agents to produce diabetes allows carrying out detailed studies of the biochemical and morphological events that occur during and after induction of a diabetes state (Lenzen, S., 2008 and Szkudelski, T., 2001). One of the chemical agents more used for inducing diabetic neuropathy is streptozotocin (STZ). This is a substance relatively selective for the beta cells of the pancreas, responsible for the production of insulin, which in certain species causes permanent diabetes. STZ enters the cell by means of a glucose transporter ($GLTU_2$) that is found in the cell membrane. It subsequently acts in the nucleus, causing the DNA alkylation and eventually the death of the beta cell, with a consequent decrease in the production of insulin and increase of glucose in the blood.

Once the diabetic pathology is established, the histology in the extremities of these animals shows a reduction in the size of the nerve fibers, axons and myelin sheath. The nerve damage causes a reduction in motor and sensory nerve conduction and tactile allodynia.

Induction of Diabetes

Figure 1:
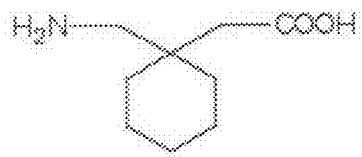
FIG. 1 shows the chemical structure of gabapentin.
Figure 2:
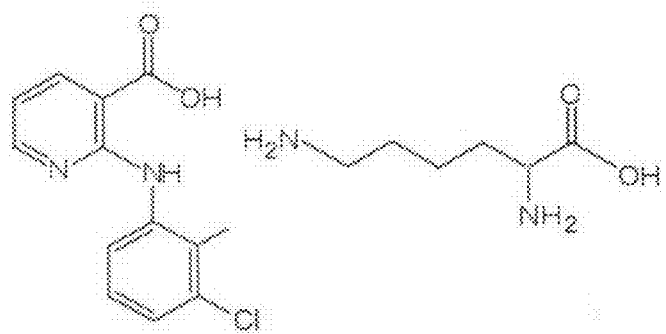
FIG. 2 shows the chemical structure of lysine clonixinate.
Figure 3:
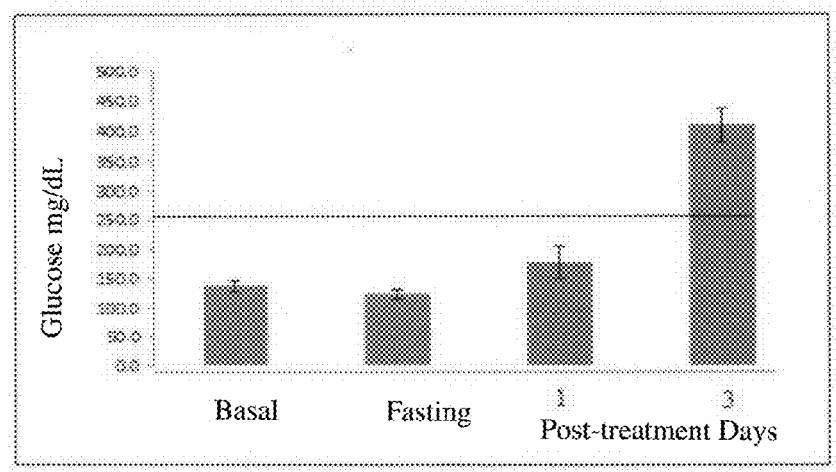
FIG. 3 is a graph showing the inducement of diabetes in mice.

In this example, a model of neuropathic pain induced by streptozotocin in male BALB/c mice 6-8 weeks of age is used. The procedure used was based on one described and widely validated (Ahlgren, S. C. and Levine, J. D., 1993), which consists in an intraperitoneal injection of streptozotocin (45 mg/kg) in 0.2 mL of saline solution. With this treatment, most of the mice developed diabetes on the third day. The blood glucose levels were evaluated in 4 groups of mice with the following characteristics: 1) without treatment (basal), 2) with treatment in fasting, 3) after 1 day of treatment and 4) after 4 days of treatment. As a diabetes parameter, a plasma glucose level≥200 mg/dL was taken. FIG. 3 shows that on the third day the majority of the mice developed diabetes, considering that the glucose levels significantly increased to 409±27.2 mg/dL in comparison with the basal levels of approximately 138.9±9.9 mg/dL. The results in each group represent the mean and standard error with an n of 10 mice.

Evaluation of Mechanical Allodynia by the Von Frey Filaments Assay

Allodynia was determined by mechanical stimulation through progressively lower application of different forces with Von Frey filaments of different caliber. The mice were placed in plastic cylinders on a wire mesh table for 15 minutes, ensuring that they were calm, and subsequently the filaments were progressively applied to the side of the leg. The filament of 0.02 g of force was the first to be applied to the left leg, five times during a total period of 30 seconds (approximately 2 seconds per stimulus), the reaction of the mouse being determined after each application. The response observed is the withdrawal or licking of the leg. If three of the five stimuli are observed, the reaction is considered positive and the mechanical threshold of the response is established.

Figure 4:
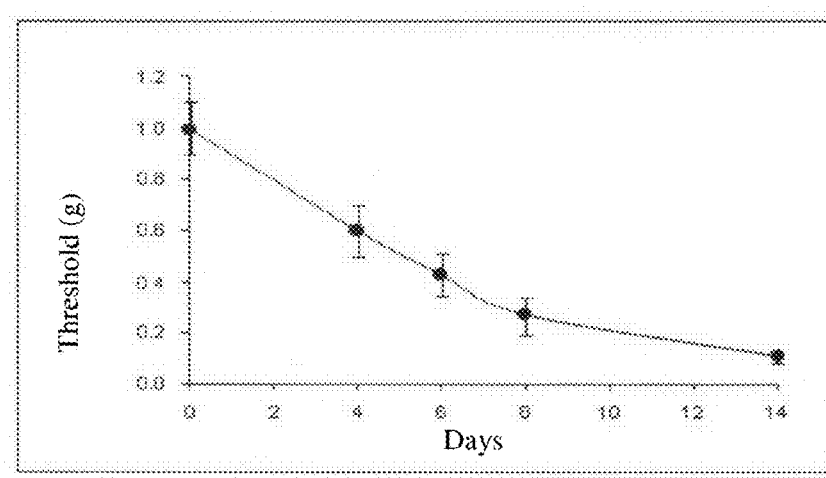
FIG. 4 is a graph showing the decrease in threshold of mechanical response in mice plotted against time.

Once diabetes is established (glucose levels over 200 mg/dL), the Von Frey filaments assay was repeated up to 14 days later, when virtually all the mice showed a significant decrease in the threshold of mechanical response. FIG. 4 shows the follow-up on the mice up to day 14, in which the threshold of mechanical response became less than 0.016 g, which indicates the establishment of allodynia. The results in each group represent the mean and standard error with an n of 10 mice.

Administration of the Drugs Individually and the CLG Combination

Different groups were used to characterize the dose-response curve of the analgesics, administering the drugs after inducing of diabetes. The doses for gabapentin were 50, 100 and 150 mg/kg, and for lysine clonixinate they were 75, 150 and 300 mg/kg. Groups of animals were used with n≥8. A 0.9% saline solution was administered by intraperitoneal route as a control of each experimental group.

For determination of antiallodynic efficacy, the mean threshold in each group was plotted as a function of time after the administration of the drugs individually or in combination, and the area below the curve (ABC) was obtained using the trapezoid rule. The percentage increase of the threshold was calculated using the following equation:

$$\% \text{ increase in threshold} = 100 \times \left(\frac{ABC \text{ threshold with drug}}{ABC \text{ threshold without drug}}\right) - 100.$$

To evaluate the net antiallodynic effect, the area under the curve of the time courses evaluated at 4 hours post-treatment was obtained. The percentage of these data in comparison with the group without treatment, in accordance with the above equation, was quantified as the antiallodynic effect.

Figure 5:
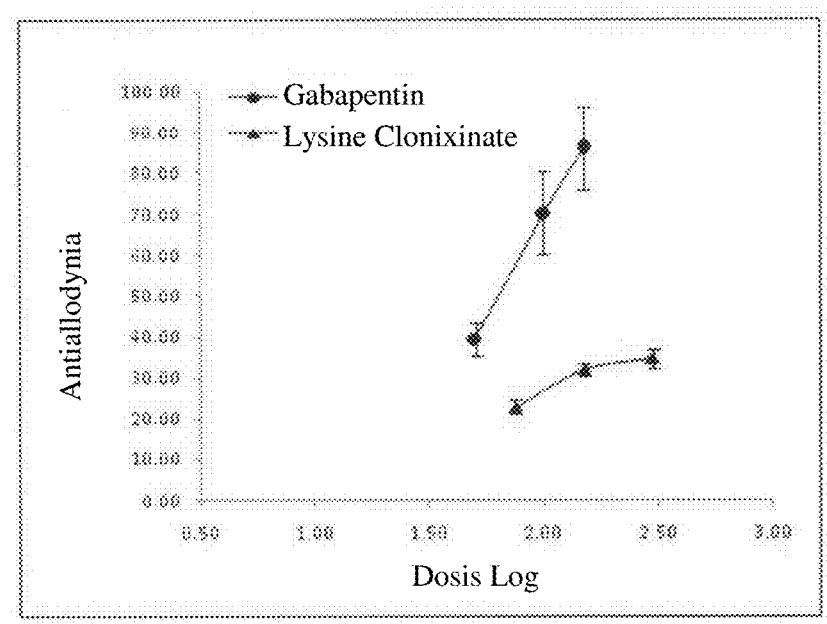
FIG. 5 is a graph showing the dose antiallodynic effect curves corresponding to gabapentin and lysine clonixinate administered individually.

FIG. 5 represents the dose-antiallodynic effect curves corresponding to gabapentin and lysine clonixinate administered individually. In both curves, a dose-dependent increase in the antiallodynic effect is observed. For gabapentin, this increase is similar to other reported studies in rodents (Kusunose, N., Koyanagi, S., Hamamura, K., et al., 2010). For lysine clonixinate, there are no reports in rodents. However, in this study found, a moderate antiallodynic effect was found. The data represent the mean and standard error of 8 mice.

From the dose-response curves, by oral administration of the drugs individually, the effective dose values that provide an analgesic effect of 30% ($DE_{30}$) were obtained for each drug. For gabapentin, the $DE_{30}$ obtained was 39.62±1.35 mg/kg, and for lysine clonixinate the $DE_{30}$ was 150.41±25.49 mg/kg.

To evaluate the effect of the CLG combination in relation to the effect of each drug individually, isobolographic analysis was used. This method is based on comparing the specific doses that are equally effective. From the respective $DE_{30}$ of the individual drugs, combinations of gabapentin and CL in fixed proportions were made and evaluated. Table 1 shows the different doses combinations used.

TABLE 1

Dose combinations of gabapentin and lysine clonixinate in fixed proportions of each drug.

| Gabapentin (mg/kg) | Lysine Clonixinate (mg/kg) | CLG combination (mg/kg) |
|---|---|---|
| $DE_{30}$ | $DE_{30}$ | |
| 39.62 | 150.41 | |
| $DE_{30}/2$ | $DE_{30}/2$ | $DE_{30}/2 + DE_{30}/2$ |
| 19.81 | 75.20 | 95.02 |
| $DE_{30}/4$ | $DE_{30}/4$ | $DE_{30}/4 + DE_{30}/4$ |
| 9.91 | 37.6 | 47.5 |
| $DE_{30}/6$ | $DE_{30}/6$ | $DE_{30}/6 + DE_{30}/6$ |
| 6.6 | 25.07 | 31.67 |
| $DE_{30}/8$ | $DE_{30}/8$ | $DE_{30}/8 + DE_{30}/8$ |
| 4.95 | 18.8 | 23.75 |

Figure 6:
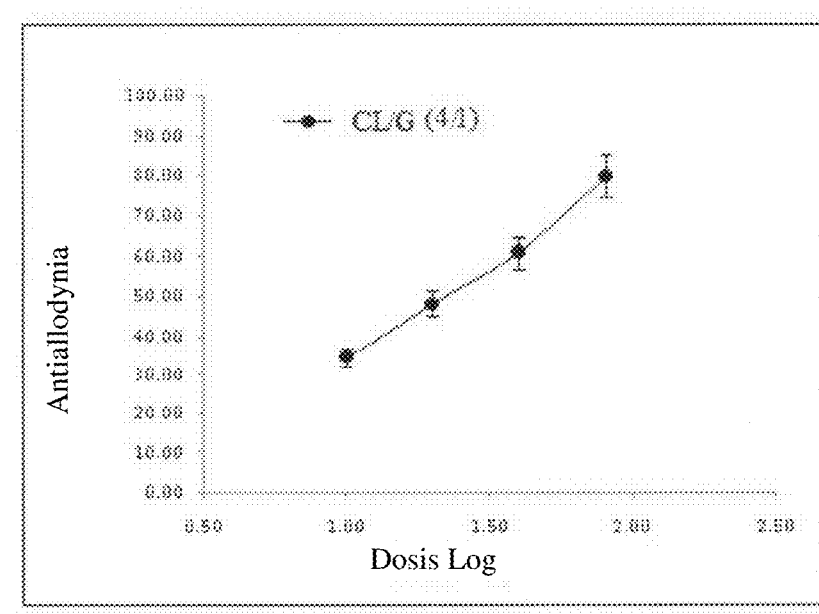
FIG. 6 is a graph showing a dose antiallodynic effect curve corresponding to gabapentin and lysine clonixinate co-administered.

Subsequently, a dose-response curve was plotted after coadministration of the two drugs. FIG. 6 shows the dose-response curve corresponding to the CLG combination. The data represent the mean and the standard error of 8 mice. From the dose-response curve of the combination of drugs, the experimental $DE_{30}$ of 8.52 mg/kg was obtained. Then the additive theoretical $DE_{30}$ of the CLG combination with its respective variance was calculated by the method reported by R. J. Tallarida (2000):

$$DE_{30} \; CLG = [(DE_{30} \text{ gabapentin} + DE_{30} \text{ lysine clonixinate})]/2$$

$$DE_{30} \; CLG = [(39.62 \text{ mg/kg}) + (150.41 \text{ mg/kg})]/2$$

$$DE_{30} \; CLG = 95.02 \text{ mg/kg}$$

Once the $DE_{30}$ values, both the theoretical and experimental, were obtained, a statistical comparison of the additive theoretical point and the experimental $DE_{30}$ value was done using a Student's t-test. The type of interaction between the two drugs was established by constructing an isobologram as follows. For each of the individual agents, the dose that produces 30% of antiallodynic effect ($DE_{30}$) was plotted in rectangular coordinates (x, y). The line that connects these two points is termed "isobolic" or the "additivity line," and on this line are all the possible combinations of the two drugs that produce only an additivity or summation effect.

Figure 7:
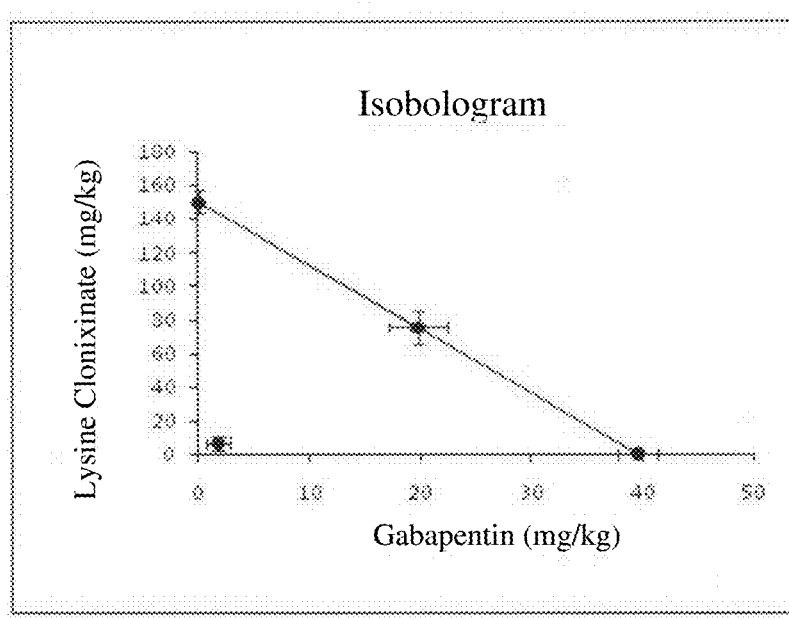
FIG. 7 is an isobologram of the combination of lysine clonixinate with gabapentin.

Now, if the experimental point falls above this additivity line, it is said that there was antagonism to the coadministration of the two drugs. But if the experimental point falls below this line, it is said that the combination of drugs produced potentiation of the effect evaluated. FIG. 7 shows the isobologram of the CLG combination. It can be seen that the interaction of gabapentin with lysine clonixinate is of the synergistic type, given that the experimental $DE_{30}$ is below the isobolic line that represents the various possible addition combinations.

To describe the magnitude of the interaction, the interaction index value ($\gamma$), which is a quantitative measure of the interaction between two drugs, was calculated:

$$\gamma = \frac{\text{Experimental } DE_{30} \text{ of combination}}{\text{Theoretical } DE_{30} \text{ of combination}}$$

The interaction index describes the experimental $DE_{30}$ as a fraction of the additive $DE_{30}$. Values near 1 indicate additive interaction, values greater than 1 imply antagonistic interaction, and values less than 1 indicate potentiation. The interaction index in this case was 0.089, which means that the experimental $DE_{30}$ was significantly lower than the additive theoretical $DE_{30}$ ($p<0.05$). So, it is considered that the combination of gabapentin and lysine clonixinate has a synergistic analgesic interaction.

According to the results in this diabetic neuropathy pain model, it was found that the combination of gabapentin and lysine clonixinate in a proportion of 1:4 produces analgesia with a potentiation of approximately 11.14 times. This may be due to the fact that different mechanisms of analgesic action are involved, gabapentin exerting an effect on the voltage-dependant calcium channels and, as mentioned, lysine clonixinate possibly exerting an effect on other types of enzymes such as nitric oxide synthase (Di Girolamo, G., Farina, M., Ribeiro, M. L. et al., 2003).

EXAMPLE II

Analgesia of the CLG Combination in the Experimental Model of Neuropathic Pain Due to Injury of the Sciatic Nerve in Mice To evaluate the analgesic efficacy of the CLG combination in neuropathic pain due to injury to the nerve, an experimental model of neuropathic pain due to ligation and cutting of sciatic nerve in mice was used. The procedure used was based on that described by I. Decosterd and C. J. Woolf (2000), which consists of isolating, tying and injuring the sciatic nerve of the mouse, followed by evaluation of the mechanical allodynia resulting from damage to the nerve.

Surgical Procedure

The surgery consisted of making an incision of approximately 1 cm in the direction proximal longitudinal to the knee and afterwards opening the skin by blunt dissection and separating the muscular layer by dissection lateral to the blood vessel near the femur. Then the right sciatic nerve was exposed under the muscles, separating them with care to display the sciatic nerve in the region where it branches from the sural nerve. Only the sciatic nerve was sutured with No. 6 thread, trying not to damage the sural nerve in any way. A tight surgical knot was made on the sciatic nerve by cutting below the suture with a pair of tweezers, then stitching the muscle layer and the skin by surgical knots. This traumatic process promptly generates allodynia, given that the day after the operation the mouse already presents a decrease of the mechanical threshold. Consequently, the antiallodynic effect of the drugs is evaluated from the second or third day after the surgery. For validation of the model, as a surgery control group, a sham surgery was used, in which the sciatic nerve is only exposed surgically, without ligation or cutting, and then the muscle tissue and skin is stitched.

Evaluation of Mechanical Allodynia by the Von Frey Filaments Assay

In all groups, the evaluation of mechanical allodynia with the application of Von Frey filaments was done in the same manner as described above for the model of pain due to diabetic neuropathy. The response thresholds in both legs, ipsilateral (right) and contralateral (left), were evaluated.

Figure 8:
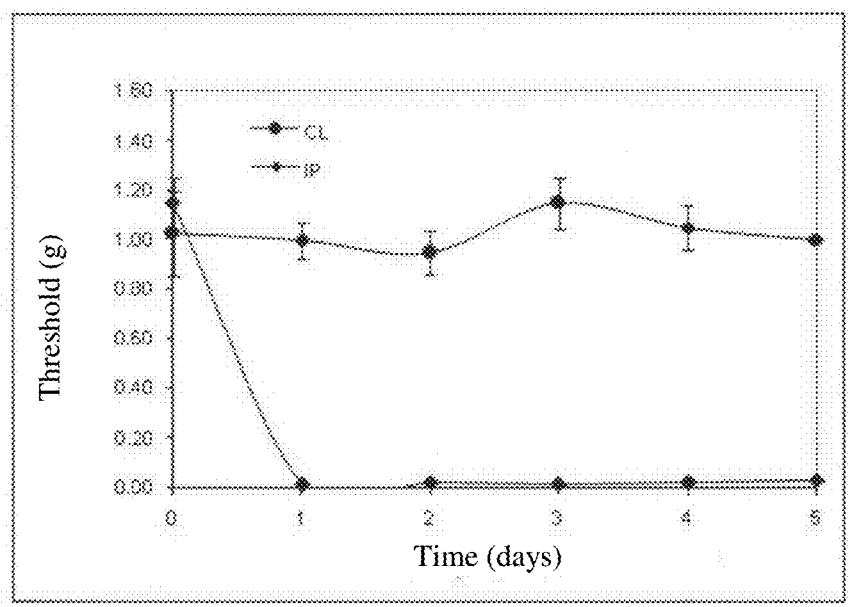
FIG. 8 is a graph of the response threshold plotted against time for the ipsilateral (IP) leg and the contralateral (CL) leg of a mouse subject.

In a group of intact mice, the threshold response was evaluated in both limbs during 5 days, without observing changes in response over time or between the extremities. In another group, the surgery of ligation and cutting of the nerve in the right (ipsilateral) leg was performed, while the left (contralateral) leg was not touched. The mechanical allodynia in both legs was evaluated once during 5 days. FIG. 8 clearly shows how there is a significant reduction in the response threshold in the surgery (ipsilateral) group, a condition that persisted until the fifth day. The data represent the mean and standard error of 8 mice.

Figure 9:
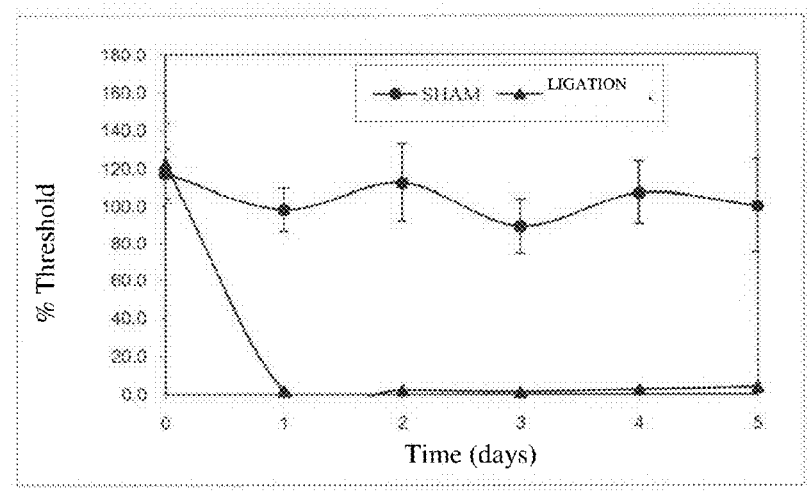
FIG. 9 is a graph of the percentage threshold plotted against time for mouse subjects having a ligation surgery and for those having a sham surgery.

To ensure the efficacy of the ligation of the nerve and to demonstrate that the allodynia is generated only by damage to the nerve and not by the surgical procedure, in another group of mice the response threshold in both legs of the mouse was determined. However, one of them underwent fake or simulated (sham) surgery, a situation where the sciatic nerve is only exposed without damage. FIG. 9 shows the time courses of the threshold percentage in both legs after a surgery of ligation and cutting of the sciatic nerve (ipsilateral) and a fake surgery (contralateral). It can be seen that reduction of the response threshold occurs in the ipsilateral leg. The data represent the mean and standard error of 8 mice.

Administration of the Drugs Individually and in Combination

For systemic administration of the drugs individually and in combinations in the mechanical allodynia model, different groups were used to characterize the dose-response curve by administering the drugs on the third day after the surgery. The doses for gabapentin were 50, 100 and 150 mg/kg, and for lysine clonixinate they were 75, 150 and 300 mg/kg. Afterwards, as described below, other groups were administered different doses of the CLG combination. Both gabapentin and lysine clonixinate and their combinations were dissolved in a 0.9% saline solution. Groups of animals were used with an experimental n of 6 to 8. A 0.9% saline solution was administered by intraperitoneal route to an experimental control group.

Figure 10:
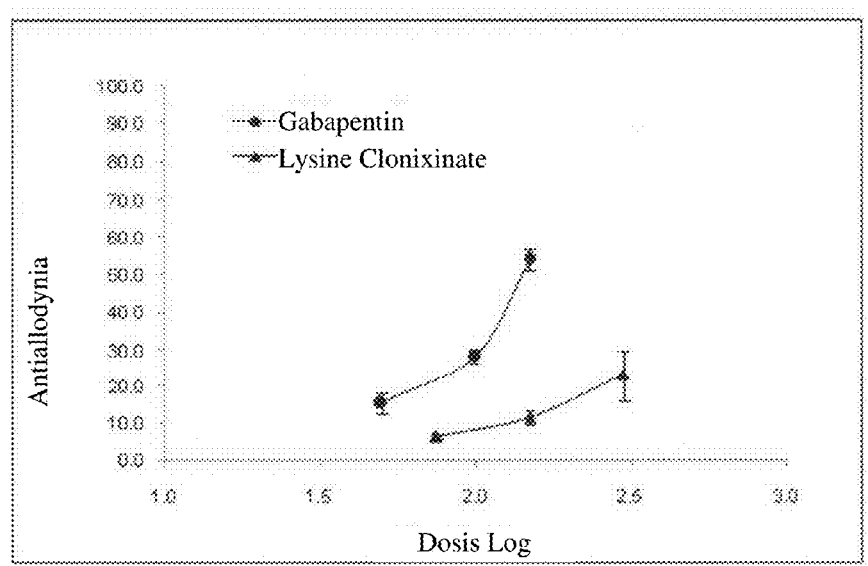
FIG. 10 is a graph showing the dose antiallodynic effect curves corresponding to gabapentin and lysine clonixinate after individual intraperitoneal administration.
Figure 11:
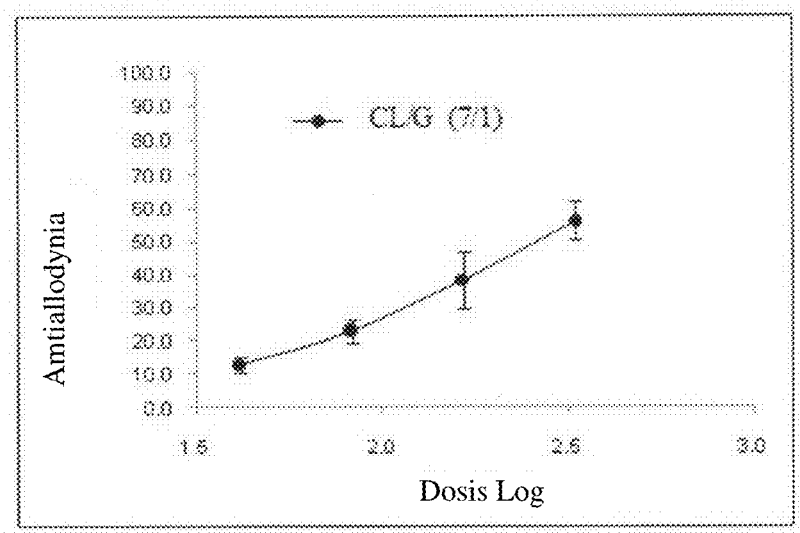
FIG. 11 is a graph showing the dose antiallodynic effect curve corresponding to gabapentin and lysine clonixinate co-admininstered intraperitoneally.

The curves in FIG. 10 represent the time course of the percentage of the antiallodynic effect after intraperitoneal administration of gabapentin and lysine clonixinate, respectively. In both curves, a dose dependent increase is observed in the antiallodynic effect. In the same way as for the diabetic neuropathy model, for gabapentin this increase is similar to other reported studies in rodents (Kusunose, N., Koyanagi, S., Hamamura, K., et al., 2010), while lysine clonixinate had a moderate antiallodynic effect, which had not been reported previously.

To evaluate the net antiallodynic effect, the area under the curve of the time courses evaluated at 4 hours post treatment, both of the ipsilateral and the contralateral leg, was obtained using the trapezoid rule. The percentage of these data was quantified as the antiallodynic effect. FIG. 10 represents the dose-antiallodynic effect curves, corresponding to gabapentin and lysine clonixinate administered individually. By means of linear regression, the $DE_{30}$ values of the drugs administered individually were obtained. For gabapentin, the $DE_{30}$ obtained was 83.82 mg/kg. For lysine clonixinate, the $DE_{30}$ was 579.67 mg/kg.

In the same way as was done in the previous model, isobolographic analysis was used to evaluate the effect of the CLG combination in relation to the effect of each drug individually. From the respective $DE_{30}$ of the individual drugs, combinations of gabapentin and CL in fixed proportions were evaluated. Table 2 shows the different doses combinations used.

TABLE 2

Dose combinations of gabapentin and lysine clonixinate in fixed proportions for each drug.

| Gabapentin mg/kg | Lysine Clonixinate mg/kg | CLG combination mg/kg |
|---|---|---|
| $DE_{30}$ 83.82 | $DE_{30}$ 579.67 | |
| $DE_{30}/2$ 41.91 | $DE_{30}/2$ 289.84 | $DE_{30}/2 + DE_{30}/2$ 331.75 |
| $DE_{30}/4$ 20.96 | $DE_{30}/4$ 144.92 | $DE_{30}/4 + DE_{30}/4$ 165.87 |
| $DE_{30}/6$ 13.97 | $DE_{30}/6$ 96.61 | $DE_{30}/6 + DE_{30}/6$ 110.58 |
| $DE_{30}/8$ 10.48 | $DE_{30}/8$ 72.46 | $DE_{30}/8 + DE_{30}/8$ 82.94 |

The evaluation of the effect of the combination of gabapentin and lysine clonixinate in this neuropathic pain model is shown in Graph 11, which shows the time curse of the antiallodynic percentage after intraperitoneal administration of the combination of the two drugs in a constant proportion at variable doses. The graph shows a dose-dependent effect of the combination. The data represent the mean and standard error of 5 to 8 mice.

From the dose-response curve of the combination of drugs, the value of the experimental $DE_{30}$ of the CLG combination was calculated and was 137.46 mg/kg. Then the additive theoretical $DE_{30}$ of the CLG combination with its respective variance was calculated by the method reported by R. J. Tallarida (2000):

$$DE_{30}\ CLG = [(DE_{30}\ \text{gabapentin} + DE_{30}\ \text{lysine clonixinate})]/2$$

$$DE_{30}\ CLG = [(83.82\ \text{mg/kg}) + (579.67\ \text{mg/kg})]/2$$

$$DE_{30}\ CLG = 331.74\ \text{mg/kg}$$

Once the $DE_{30}$ values, both the theoretical and experimental, were obtained, a statistical comparison was done using a Student's t-test. This test showed that experimental $DE_{30}$ (137.46 mg/kg) is significantly lower than the additive theoretical $DE_{30}$ (331.74 (mg/kg), with a value of p<0.05.

Figure 12:
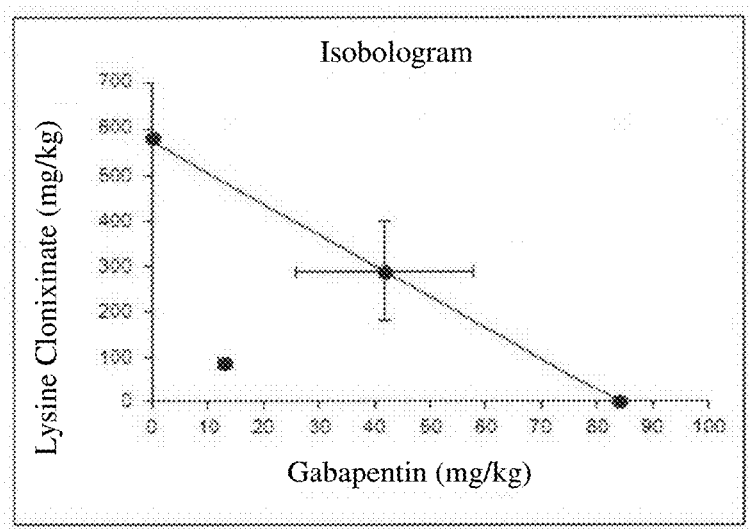
FIG. 12 is an isobologram of the intraperitoneal co-administration of lysine clonixinate with gabapentin.

FIG. 12 shows the isobologram. It can be seen that the interaction of gabapentin with lysine clonixinate is of the synergistic type, given that the experimental $DE_{30}$ is below the isobolic line that represents the addition combinations.

In the same way as for the diabetic neuropathy model, to describe the magnitude of the interaction the value of the interaction index (γ) is calculated:

$$\gamma = \frac{\text{Experimental } DE_{30} \text{ of } CLG \text{ combination}}{\text{Theoretical } DE_{30} \text{ of } CLG \text{ combination}}$$

The interaction index in this case was 0.311, so the type of interaction of gabapentin with lysine clonixinate also produced an analgesic synergy between the drugs in this neuropathic pain model, although not of the same magnitude as in the case of diabetic neuropathy pain, in which the interaction index was 0.089.

Furthermore, to know the antiallodynic effect evaluated in this neuropathic pain model using other proportions, the combinations shown in Table 3 were selected:

TABLE 3

Dose combinations of gabapentin and lysine clonixinate in different proportions of each drug.

| Gabapentin mg/kg | Lysine Clonixinate mg/kg | CL/G combination mg/kg |
|---|---|---|
| 100 | 50 | 50/100 |
| 100 | 100 | 100/100 |
| 100 | 150 | 150/100 |

Figure 13:
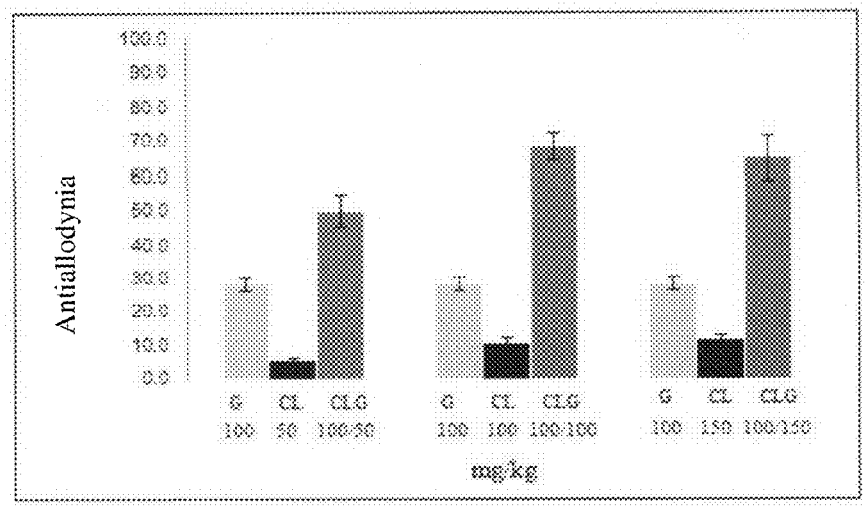
FIG. 13 is a graph showing allodynic effect produce by co-administration of lysine clonixinate ang gabapentin in different dose combinations.

As shown in FIG. 13, all proportions used produce an antiallodynic effect that is significantly greater than that produced by the drugs administered separately. The data represent the mean±standard error of 8 determinations. In all the cases a value of p<0.05 according to the Student's t-test was obtained.

Evaluation of the Toxicological Effects of the CLG Combination

To investigate possible toxic effects by subchronic administration (14 days) of gabapentin, lysine clonixinate and their combination, studies were done to evaluate motor activity and neurological profile, as well as some blood biochemical markers, hepatic damage and kidney damage. The motor activity and biochemical profile evaluation data were evaluated by an analysis of variance (ANOVA), followed by a Dunnett test. The neurological profile data were evaluated by grading, with 0=null, 1=moderate and 3=significant.

Four experimental groups of 10 mice each were used, to which the following doses were administered by intraperitoneal route: 1) 0.9% saline solution, 2) gabapentin 31 mg/kg, 3) lysine clonixinate 150 mg/kg, 4) combination of gabapentin 31 mg/kg plus lysine clonixinate 150 mg/kg. This administration was done consecutively every 24 hours. After 14 days of exposure, toxicological tests were done.

Figure 14:
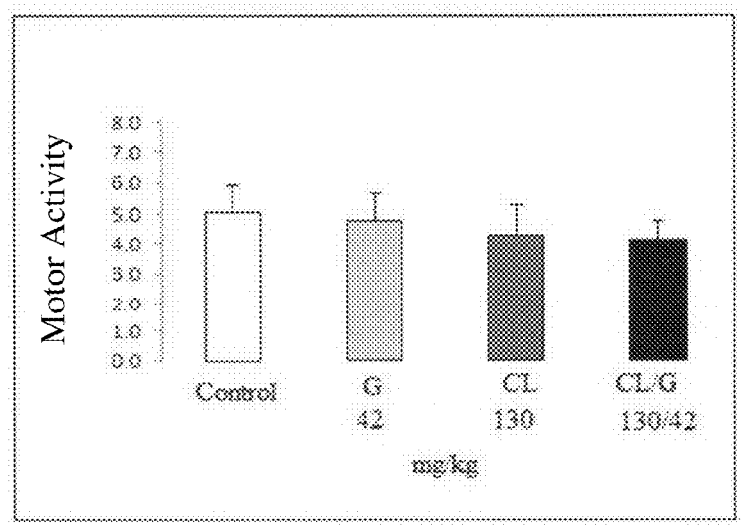
FIG. 14 is a graph showing effects on motor activity of mouse subjects to a control, individual administration and co-administration of lysine clonixinate and gabapentin.

Among the tests performed, the motor activity of the mice was evaluated, since it that represents, in many cases, an assertive way to evaluate damage to systems regulated by some systems of neurotransmitter such as dopamine and others that control posture and movement. In this study, the number of times that the mice cross 2 zones of a cylinder of 20 cm diameter in 1 minute was evaluated. FIG. 14 shows the effect of exposure to: 1) control (0.9% saline), 2) gabapentin 31.09 mg/kg, 3) lysine clonixinate 150.41 mg/kg and 4) the CLG combination 150/31 mg/kg during 14 days.

The data represent the mean and standard error of 10 mice for each one of the different treatments. The results showed no statistically significant change in the activity due to the different drug exposures in comparison with control mice that received only saline solution.

A daily evaluation was simultaneously done of the neurological profile, since one critical aspect in all experimental models of nervous system pathologies is evaluation of the final neurological prognosis. In the case of subchronic administration of medication, evaluation of the final functional deficit is a valuable tool. Therefore, after receiving a daily dose for 14 days, the mice underwent an evaluation of the neurological profile of the experimental animals.

This evaluation included parameters such as behavior, reflexes, convulsions and motor coordination. Each parameter was graded on a scale of 0=null, 1=slight, 2=moderate and 3=considerable.

Table 3 shows the results of this evaluation after the administration of each drug: gabapentin (31.09 mg/kg) and lysine clonixinate (150.41 mg/kg) and the CLG combination, in addition to a control group managed with saline solution.

As can be seen in Table 4, no significant interaction is noted in any of the parameters evaluated, in the 14 days that the treatment lasted. The value of all the parameters was equal to 0, that is, absent, indicating that, at these doses, neither gabapentin, lysine clonixinate, nor their combination causes neurological damage.

TABLE 4

Dose combination of gabapentin and lysine clonixinate in fixed proportions of 0.5 of each drug.

| Treatment | Control | Gabapentin 31 mg/kg | Lysine Clonixinate 150 mg/kg | Gabapentin 31 mg/kg Lysine Clonixinate 150 mg/kg |
|---|---|---|---|---|
| Behavior | | | | |
| Irritability | 0 | 0 | 0 | 0 |
| Vocalization | 0 | 0 | 0 | 0 |
| State of Alert | 0 | 0 | 0 | 0 |
| Exploratory Activity | 0 | 0 | 0 | 0 |
| Flabbiness | 0 | 0 | 0 | 0 |
| Straightening of Tail | 0 | 0 | 0 | 0 |
| Reflexes | | | | |
| Corneal | 0 | 0 | 0 | 0 |
| Convulsions | | | | |
| Tonic | 0 | 0 | 0 | 0 |
| Clonic | 0 | 0 | 0 | 0 |
| Gait Movements | 0 | 0 | 0 | 0 |
| Jumping Movement | 0 | 0 | 0 | 0 |
| Motor Coordination | | | | |
| Staggering Gait | 0 | 0 | 0 | 0 |
| Abnormal Gait | 0 | 0 | 0 | 0 |
| Running in Circles | 0 | 0 | 0 | 0 |
| Paralysis | 0 | 0 | 0 | 0 |

Finally, laboratory tests were done to know if there were any changes in blood chemistry or significant changes in hepatic and renal function markers, since both the liver and the kidneys are a frequent target of many drugs, which can cause significant damage in the structure and/or function of these organs. The levels of glucose, total proteins, the enzymes glutamate oxaloacetate transaminase (GOT) and glutamate pyruvate transaminase (GPT), creatinine and urea were evaluated in the mice that were administered, during 14 days, gabapentin (31.09 mg/kg), lysine clonixinate (150.41 mg/kg) and the CLG combination (150/31 kg/mg).

The results of the laboratory analyses revealed that there were no changes in the levels of glucose or in the concentration of plasma proteins in the 14 days of treatment.

In none of the hepatic function markers (GOT and GPT) or in the creatinine and urea levels was any statistically significant modification noted in comparison with the control group. Each group used 10 mice.

CONCLUSIONS

The treatment of neuropathic pain is complex, whether it is caused by an injury to the nerve or manifests itself as a result of a disease such as diabetes mellitus. Often this type of pain is treated with medicines that act on the CNS and have limited therapeutic effects with adverse effects when administered at high doses. For example, it has been reported that gabapentin shows efficacy in the treatment of diabetic neuropathy and post-herpetic neuralgia at effective doses of up to 1800 to 3600 mg per day. The most common adverse effects are at the level of the CNS, since it has been reported that more than 10% of patients treated with gabapentin show drowsiness, dizziness, ataxia, headache and fatigue. Other adverse effects also frequently reported are vertigo, hyperkinesia, paresthesia, alterations in reflexes, anxiety and hostility.

To try to improve analgesic efficacy, combinations of two or more drugs have been made. However, the majority of these have added to the adverse effects, which, in general, lead to depression of the CNS.

In the present study, we used two mouse models to study neuropathic pain: the model of diabetic neuropathy induced by streptozotocin and the model of neuropathic pain induced by a physical injury to the sciatic nerve. Both models served to demonstrate the efficacy of the combination of gabapentin and lysine clonixinate administered by intraperitoneal route. In the diabetic neuropathy model, it was found that the combination of gabapentin/lysine clonixinate in a ratio of 1:4 provides close to 80% relief of neuropathic pain in mice.

The analgesic potency of the CLG combination, evaluated by isobolographic analysis in which the experimental $DE_{30}$ was compared with the additive $DE_{30}$, and the resulting interaction index ($\gamma=0.089$) demonstrated in this model that the CLG combination presents an analgesic synergy approximately 11 times greater than that of the individual drugs. In the model of neuropathic pain due to injury to the nerve, it was found that the combination of gabapentin/lysine clonixinate in a ratio of 1:7 presents an analgesic potency, and the isobolographic analysis demonstrated a synergy between both drugs with an interaction index value $\gamma$ equal to 0.311. In this model, the analgesic effect was approximately 3 times greater than that of the individual drugs. It was also found that the ratios of gabapentin/lysine clonixinate equal to 100/50 mg/kg (1:0.5), 100/100 mg/kg (1:1) and 100/150 mg/kg (1:1.5) mg/kg provided relief of neuropathic pain in mice.

It should be noted that, according to the results obtained with regard to the effect of gabapentin in other models of neuropathic pain, these coincide closely with the maximum effect found with a dose of 150 mg/kg (Naoki, K., Koyanagi, S., Hamamura, K., et al. 2010). On the other hand, it has been reported that nonsteroidal analgesics have a limited effect on this type of pain. Nevertheless, in the studies performed, we found a moderate effect of up to 30% of the effect with lysine clonixinate. However when we evaluated the CLG combination, an important synergy was observed in both models, being greater in the case of diabetic neuropathy. In the present study, it was possible to show that, under the experimental conditions described, the CLG combination does not show adverse effects on motor activity or alterations in neurological parameters. Nor were significant changes found in some biochemical markers that indicate hepatic or renal damage or in hematologic characteristics at least during 14 days of daily exposure to the drugs.

In conclusion, the results of this work demonstrate that the combination of gabapentin and lysine clonixinate, mixed at doses equivalent to those used clinically with the individual drugs, provides relief of neuropathic pain of 70% to 80%. Also, depending on the origin of the neuropathic pain, the CLG combination has an analgesic potency 3 to 11 times greater than that of the individual drugs. Therefore, it can be concluded that the CLG combination represents a therapeutic alternative for the treatment of neuropathic pain without the serious adverse effects of other combinations for the treatment of this type of pain.

BIBLIOGRAPHY

Ahlgren, S. C., Levine, J. D. "Mechanical hyperalgesia in streptozotocin-diabetic rats." *Neuroscience.* 1993; 52:1049-55.

Attal, N. and Finnerup, N. B. "Pharmacological management of neuropathic pain," IASP: International Association for the Study of Pain, Pain Clinical Updates. 2010, 18:9:1-8.

Bouhassira, D., Lanteri-Minet, M., Attal, N., Laurent, B. and Touboul, C. "Prevalence of chronic pain with neuropathic characteristics in the general population." *Pain.* 2008; 136:380-7.

Chaparro, L. E., Smith, S. A., Moore, R. A., Wiffen, P. J., Gilron, I. "Pharmacotherapy for the prevention of chronic pain after surgery in adults." *Cochrane Database of Syst. Rev.* 2013, Issue 7.

Decosterd, I. and Woolf, C. J. "Spared nerve injury: an animal model of persistent peripheral neuropathic pain." *Pain.* 2000; 87 (2), 149-158.

DiGirolamo, G., Farina, M., Ribeiro, M. L., Ogando, D., Aisemberg, J., de los Santos, A. R., Marti, M. L. and Franchi, A. M. "Effects of cyclooxygenase inhibitor pretreatment on nitric oxide production, nNOS and iNOS expression in rat cerebellum." *British Journal of Pharmacology.* 2003; 139:1164-1170.

Dworkin, R., O'Connor, A., Audette, J., Baron, R., Gourlay, G., Haanpaa, M., Kent, J., Krane, E., LeBel, A., Levy, R., Mackey, S., Mayer, J., Miaskowski, C., Raja, S., Rice, A., Schmader, K., Stacey, B., Stanos, S., Treede, R. D., Turk, D., Walco, G. and Wells, C., *Recommendations for the Pharmacological Management in Neuropathic Pain: An Overview and Literature Update*, Mayo Clin Proc. 2010; 85(3) (Suppl): S3-S14.

Finnerup, N. B., Sindrup, S. H., Jensen, T. S. "The evidence for pharmacological treatment of neuropathic pain." *Pain.* 2010; 150:573-81.

Gordh, T. E., Stubhaug, A., Jensen, T. S., Arnèr, S., Biber, B., Boivie, J., Mannheimer, C., Kalliomäki, J, Kalso, E. "Gabapentin in traumatic nerve injury pain: a randomized, double-blind, placebo-controlled, cross-over, multicenter study." *Pain.* 2008; 138:255-66.

Green, R., Flamm, S. "AGA technical review on the evaluation of liver chemistry tests." *Gastroenterol.* 2002; 123 (4), 1367-84.

Kusunose, N., Koyanagi, S., Hamamura, K., Matsunaga, N., Yoshida, M., Uchida, T., Tsuda, M., Inoue, K. and Ohdo, S. "Molecular basis for the dosing time-dependency of anti-allodynic effects of gabapentin in a mouse model of neuropathic pain." *Mol Pain. Nov.* 26, 2010; 6:83.

Lenzen, S. "The mechanisms of alloxan- and streptozotocin-induced diabetes." *Diabetologia.* February 2008; 51(2): 216-26.

Moore, R. A., Wiffen, P., Derry, S., and McQuay, H., Gabapentin for neuropathic pain and fibromyalgia in adults. *Cochrane Database Syst, Rev.* 2014; (3):1-84.

Schmidtko, A., Tegeder, I. and Geisslinger, G. "No NO, no pain? The role of nitric oxide and cGMP in spinal pain processing." *Trends in Neurosciences.* 2009; 32:339-346.

Straube, S., Derry, S., Moore, F., Wiffen, P., and McQuay H. Single dose oral gabapentin for established acute postoperative pain in adults. *Cochrane Database Syst. Rev.* 2014; (5):1-28.

Szkudelski, T. "The mechanism of alloxan and streptozotocin action in B cells of the rat pancreas." *Physiological Research*/Scientiarum Bohemoslovaca Academy. 2001; 50(6):537-46.

Tao, F., Tao, Y. X., Zhao, C., Doré, S., Liaw, W. J., Raja, S. N. and Johns, R. A. "Differential roles of neuronal and endothelial nitric oxide synthases during carrageenan-induced inflammatory hyperalgesia." *Neuroscience.* 2004; 128, 421-430

Tesfaye, S., Boulton, A. J., Dyck, P. J., Freeman, R., Horowitz, M., Kempler, P., Lauria, G., Malik, R. A., Spallone, V., Vinik. A., Bernardi, L., Valensi, P. Toronto Diabetic Neuropathy Expert Group. "Diabetic Neuropathies: update on definitions, diagnostic criteria, estimation of severity, and treatments." *Diabetes Care.* 2010; 33:2285-2293.

Tesfaye, S., Vileikyte, L., Rayman, G., Sindrup, S., Perkins, B., Baconja, M., Vinik, A. and Boulton, A. On behalf of the Toronto Expert Panel on Diabetic Neuropathy. "Painful diabetic peripheral neuropathy: consensus recommendations on diagnosis, evaluation for assessment and management." The Toronto Consensus Panel on Diabetic Neuropathy guidelines. *Diabetes Metab Res Rev.* 2011; 27: 629-638.

Treede, R. D., Jensen, T. S., Campbell, J. N., Cruccu, G., Dostrovsky, J. O., Griffin, J. W., Hansson, P., Hughes, R., Nurmikko, T. and Serra, J. "Neuropathic pain: redefinition and a grading system for clinical research purposes." *Neurology.* 2008; 70(18):1630-1635.

Vinik, A. and Casellini, C. "Guidelines in the management of diabetic nerve pain: clinical utility of pregabalin." *Dove Press Journal: Diabetes, Metabolic Syndrome and Obesity: Targets and Therapy.* 2013: 6 57-78.

Von Hehn, C. A., Baron, R. and Woolf, C. J. "Deconstructing the neuropathic pain phenotype to reveal neural mechanisms." *Neuron.* 2012; 73(4):638-52.

Winter C., Risley E. A ND Nuss G. Carrageenin-induced edema in hind paw of the rat as an assay for antiinflammatory drugs. *Proc Soc Exp Biol Med.* 1962 Dec; 111: 544-7.

Woolf, C. J. "Pain: moving from symptom control toward mechanism-specific pharmacologic management." *Ann. Intern. Med.* 2004; 140, 441-451.

Yoon, M. and Yaksh, T. "Evaluation of interaction between gabapentin and ibuprofen on the formalin test in rats." *Anesthesiology.* 1999; 91:1006-13.

Zimmermann, M. "Ethical guidelines for investigations on experimental pain in conscious animals." *Pain.* 1983; 16: 109-110.

The invention claimed is:

1. An analgesic pharmaceutical composition, comprising:
   a G component, selected from the group consisting of: gabapentin, any pharmaceutically acceptable salts thereof, and combinations thereof; and
   an LC component, selected from the group consisting of: lysine clonixinate, hydrates thereof, any pharmaceutically acceptable salts thereof, and combinations thereof;
   wherein the LC component in present in the range of from 0.5 parts to 7 parts per part of the G component.

2. The composition in accordance with claim 1, wherein the G component is the chemical compound: 2-[1-(aminomethyl)cyclohexyl]acetate.

3. The composition in accordance with claim 1, wherein the LC component is: the lysine salt of 2-(3-chloro-2-methyl-phenyl) aminopiridin-3-carboxylic acid.

4. The composition in accordance with claim 1, wherein the LC component is present, per part of the G component, in the amount selected from the group consisting of: 0.5 parts, 1 part, 1.5 parts, 4 parts or 7 parts.

5. The composition in accordance with claim 1, further comprising a pharmaceutically acceptable excipient.

6. The composition in accordance with claim 5, wherein the composition is configured to be administered as a medicine.

7. The composition in accordance with claim 6, wherein the medicine is in the form of an injectable solution.

8. The composition in accordance with claim 5, wherein the medicine is in the form of a dosage selected from the group consisting of: tablets, capsules, oral solutions, oral suspensions, gels, ointments and suppositories.

9. A method of providing therapy for pain, comprising the steps of:
   providing an analgesic pharmaceutical composition, comprising:
      a G component, selected from the group consisting of: gabapentin, any pharmaceutically acceptable salts thereof, and combinations thereof; and
      an LC component, selected from the group consisting of: Isyine clonixinate,-hydrates thereof, any pharmaceutically acceptable salts thereof, and combinations thereof:
      wherein the LC component is present in the range of from a 0.5 parts to 7 parts per part of the G component; and
      wherein the analgesic pharmaceutical composition is compounded as a dosage of medicine in a therapeutically form and amount; and
   administering the dosage to a patient in need of therapy for pain.

10. The method of claim 9, wherein the pain is of neuropathic origin.

11. The method of claim 9, wherein the pain derives from a diabetic neuropathy.

12. The method of claim 9, wherein the pain derives from an injury to a nerve.

* * * * *